United States Patent [19]

Stearns et al.

[11] Patent Number: 5,528,150
[45] Date of Patent: Jun. 18, 1996

[54] GAS SAMPLING APPARATUS INCLUDING A SEALED CHAMBER COOPERATIVE WITH A SEPARATE DETECTOR CHAMBER

[76] Inventors: Stanley D. Stearns, 1201 Archley Dr., Houston, Tex. 77055; Wayne E. Wentworth, 614 E. Larkspur Cir., Pearland, Tex. 77584

[21] Appl. No.: 349,088

[22] Filed: Dec. 2, 1994

Related U.S. Application Data

[63] Continuation-in-part of Ser. No. 662,149, Feb. 28, 1991, Pat. No. 5,153,519, Ser. No. 956,632, Oct. 5, 1992, Pat. No. 5,317,271, Ser. No. 176,968, Jan. 3, 1994, Pat. No. 5,394,092, Ser. No. 201,467, Feb. 25, 1994, Pat. No. 5,394,090, and Ser. No. 201,469, Feb. 25, 1994, Pat. No. 5,394,091.

[51] Int. Cl.$^6$ ............................ G01N 27/62; G01N 27/68
[52] U.S. Cl. ........................ 324/464; 324/455; 73/28.02
[58] Field of Search ............................. 324/71.4, 123 R, 324/449, 450, 452, 464; 73/28.02, 23.35; 250/379, 385.2; 313/231.41, 231.71; 315/111.01, 111.91; 436/153

[56] References Cited

U.S. PATENT DOCUMENTS

| | | | |
|---|---|---|---|
| 3,540,851 | 11/1970 | Vree et al. ............................ 324/464 X |
| 3,679,973 | 7/1972 | Smith, Jr. et al. .................... 324/464 X |
| 4,724,394 | 2/1988 | Langer et al. ............................ 324/464 |
| 4,851,683 | 7/1989 | Yang et al. ............................... 250/339 |
| 5,153,519 | 10/1992 | Wentworth et al. ..................... 324/464 |
| 5,317,271 | 5/1994 | Wentworth et al. ..................... 324/464 |
| 5,338,931 | 8/1994 | Spangler et al. ......................... 250/287 |
| 5,394,090 | 2/1995 | Wentworth et al. ..................... 324/464 |
| 5,394,091 | 2/1985 | Wentworth et al. ..................... 324/464 |
| 5,394,092 | 2/1995 | Wentworth et al. ..................... 324/464 |

OTHER PUBLICATIONS

A Compilation of Research on Pulsed Discharge Detectors, Article, Summary of Paper Presented at the Pittsburgh Conference, 1994, month unavailable.

Introduction to: Pulsed Discharge Helium Ionization Detector, Reprint of Publication in the Journal of Chromatographia, vol. 34, No. 5–8, pp. 219–115 (1992) month unavailable.

Introduction to: Pulsed Discharge Electron Capture Detector Reprint devoted solely to the PDECD (J of Chromatogra. Sci.), vol. 30, pp. 478–485. (1992), month unavailable.

Pulsed Discharge Helium Ionization Detector, W. E. Wentworth, S. V. Vasnin, Stearns, & Meyer, Chromatographia, vol. 34, No. 5–8, Sep./Oct. 1992.

Pulsed Discharge Photoionization Detector (PDPID), A Summary of a paper presented at the 1994–Pittsburgh Conference by W. E. Wentworth, month unavailable.

Pulsed Discharge Emission Detector–Application to Analytical Spectroscopy of Permanent Gases, Vasnin, Wentworth, Stearns & Meyer, Chromatographia, vol. 34, No. 5–8, Sep./Oct. 1992.

(List continued on next page.)

*Primary Examiner*—Kenneth A. Wieder
*Assistant Examiner*—Diep Do
*Attorney, Agent, or Firm*—Gunn & Associates

[57] ABSTRACT

An isolated detector for gas is set forth and incorporates a closed source chamber in cooperation with a sample chamber through which sample gas flows. Gas within the source chamber comprises Krypton which is excited to a metastable state by a pulsed, high voltage, direct current spark. Subsequent decay of metastable argon emits ionizing radiation which passes through a membrane window into the sample chamber thereby ionizing selected constituents within the sample gas. Charged particles resulting from the ionization of selected constituents are collected with voltage biased electrodes in the sample chamber, and the magnitude of the resulting current flow is related to the concentration of the ionized molecules or compounds. The apparatus for generating ionizing radiation requires no external source of gas, is rugged, is relatively inexpensive to manufacture and operate, and exhibits an operating life much longer than source lamps used in prior art devices. The preferred embodiment of the invention is directed to the quantitative measure of impurities or pollutants in air samples.

20 Claims, 1 Drawing Sheet

OTHER PUBLICATIONS

Pulsed Discharge Helium Ionization Detector, A Universal Detector for Inorganic Compounds at the Subpicogram Level, Wentworth, et al, Version of 5/25, undated.

Reprinted from Process Control & Quality, 5 193–204, Elsevier Science B.V., Amsterdam, Pulsed–Discharge Helium Ionization/Electron Capture/Emission Detector of Chlorinated Compounds, Wentworth, et al, Jan. 1993.

Environmental Applications of the Pulsed–Discharge Electron–Capture Detector, Wentworth, D'Sa & Cai, Journal of Chromatographic Science, vol. 30, Dec. 1992.

Introduction to: Pulsed Discharge Emission Detector (PDED) Chromatographia, vol. 34, pp. 226–234, (1992), month unavailable.

5,528,150

GAS SAMPLING APPARATUS INCLUDING A SEALED CHAMBER COOPERATIVE WITH A SEPARATE DETECTOR CHAMBER

BACKGROUND OF THE DISCLOSURE

This disclosure is a continuation in part of application Ser. No. 662,149 which was filed on Feb. 28, 1991 and which issued as U.S. Pat. No. 5,153,519 on Oct. 6, 1992, also application Ser. No. 956,632 which was filed on Oct. 5, 1992, now issued as U.S. Pat. No. 5,317,271 on May 31, 1994, application Ser. No. 176,968 which was filed on Jan. 3, 1994, now U.S. Pat. No. 5,394,092 and also application Ser. No. 201,467, now U.S. Pat. No. 5,394,090 and application Ser. No. 201,469, now U.S. Pat. No. 5,394,091 both filed Feb. 25, 1994.

The present disclosure is directed to a gas analysis apparatus which utilizes photoemission from a pulsed direct current (DC) spark transmission across the gap between a pair of spaced electrodes. More specifically, the source of photoelectric emission requires no continuous source of gas, is rugged, relatively inexpensive to construct and maintain, and possesses an extremely long operating life.

Many photoemission based gas analysis devices have been used in the past. The devices are commonly referred to as "sniffers" and the actual measuring or monitoring of sample gas is often referred to as "sniffing". These devices, however, encounter typical limitations in their operation. One such limitation is the requirement of a photoemission source which has substantial life. Most prior art devices incorporate lamps emitting radiation within a specific energy range or band. Sniffing type devices are used to monitor the atmosphere in the vicinity of benzene processing plants, refrigeration systems which may leak fluoride compounds, and other facilities from which leaks into the atmosphere are undesirable. The life of this prior art equipment is limited, and prior photoemission devices last only two or three hundred hours in regular operation. Such a limitation on the life of the photoemission lamp not only introduces economic problems in the cost to replace, but also operational problems in that monitoring or sniffing must be terminated during replacement.

U.S. Pat. No. 5,153,519 of the present inventor discloses a detector device which is used to analyze gas samples. In one embodiment, a pulsed DC spark acts on a carrier gas containing other compounds to be identified and quantified, where the carrier gas is typically helium. The charged species created by the spark are used to classify and/or quantify the unknown compounds in the carrier. This detector is connected with upstream or downstream devices such as a sample source, gas chromatograph column, spectrum analyzer or the like. A sample to be analyzed is loaded for flow along with the carrier gas into a system chamber. While the carrier gas and sample mix passes through the detection device, a pulsed, high voltage DC spark discharge to form selected charged or energized species within the gas mixture. The spark discharge simultaneously initiates several types of detection systems. For instance, a very short DC spark creates a readily available thermalized electron flux which can be used in a detection system. In an alternate aspect of operation, the spark creates a more slowly diffused flux of metastable helium atoms which drift toward selected electrodes at a controlled rate. The metastable helium atoms (over a time interval which is relatively short) upon decay act as a photoemission source thereby ionizing molecules within the sample gas which, as a secondary and delayed reaction, can be measured by the detection system. Another aspect involves photoionization of gas into positive and negative charged particles normally recombining at high speed. If a selected sweep pulse voltage is applied, the recombination is prevented to furnish a signal indicative of the unknown compounds within the gas mixture. Identification and quantification of compounds of interest can, to some extent, be controlled by varying the timing of the spark, the electrode geometry, the voltages of the detector segments, and the modes of interactions observed within the plasma. In this invention, the source of photoionization is not an external lamp but is a metastable compound, preferably helium, actually manufactured within the carrier gas-sample gas mixture by the pulsed DC spark discharge. The life of the source is, in principle, unlimited as long as an external mixture of sample gas and carrier gas is supplied and as long as the gas mixture is exposed directly to the repetitive DC spark discharge. The requirement for an external source of carrier gas causes the device to be relatively large in size thereby limiting applications and also increases the manufacturing and operating costs of the device.

This disclosure is directed toward selectively ionizing pollutants in air without ionizing the major constituents of air namely, nitrogen, oxygen, water and carbon dioxide. Selective ionization is accomplished by using a mixture of preferably helium and krypton as a carrier gas in a high voltage spark excitation and ionization chamber. The spark discharge may form or cause creation of metastable inert gas which upon decay produces photoemission below the ionization potential of the major constituents of air. The sample gas and carrier gas must continuously flow and are mixed within the ionization chamber. As in the previously referenced U.S. Pat. No. 5,153,519, the life of the photoionization "source" is predicated on a continuous supply of source gas, although selective ionization is superior, especially in applications involving the monitoring of air for pollutants.

SUMMARY OF THE PRESENT INVENTION

The present disclosure is directed to a gas analysis apparatus which incorporates photoemission from a pulsed direct current (DC) spark transmission across a gap between a pair of spaced electrodes. The spark is formed in an atmosphere which is maintained at or near prevailing atmospheric pressure thereby eliminating the need for a high vacuum system required in alternative spark discharge systems. Moreover, the spark is formed in a closed chamber, referred to hereafter as the spark chamber, which is filled with a gas which responds to the temperature gradient formed within the closed chamber at the moment of sparking. The photoemission source does not require continuous external supply of carrier gas as is required in earlier systems. When the spark occurs, photoemission occurs from the immediate region of the spark. This is accompanied with heating of the gas in the pathway of the spark. Because of this heating, the gas in the spark gap is evacuated by convective gas flow in the upward direction within the closed chamber and cooler gas replaces heated gas in the region of the spark gap. The relatively light, buoyant, heated gas moves toward the top of the chamber and mingles with unheated gas and is subsequently cooled. The sparking therefore creates a circulation of gas within the closed chamber which continuously replenishes the spark gap region with fresh gas.

The present invention further utilizes a window membrane between the spark chamber and an adjacent sample chamber. The window membrane is transparent to photoemission generated within the spark chamber. In the sample chamber, a sample gas is introduced to flow through the sample chamber and out through the sample chamber. The sample gas is thereby exposed to photoemissions which are generated within the spark chamber and pass through the window membrane separating the spark chamber from the sample chamber. The photoemission excites selected molecules within the carrier gas. Subsequent decay of these excited molecules is then detected and related to the concentrations of the selected molecules within the sample gas. One sample carrier gas is preferably air thereby providing an instrument which tests for airborne gaseous discharges.

The photoemission source of the present invention has a much longer life than prior lamp type sources, yet does not require a continuous supply of source gas as do the previously referenced discharge type sources. Furthermore, the cost of the present photoemission source is lower than earlier spark discharge devices and is comparable to the costs of relatively short lived photoemission lamps. In addition, the present photoemission source is mechanically simple and very rugged thereby reducing the chance of breakage in a hostile environment to monitoring equipment. Another feature of the present invention is that photoemission can be produced at a specified energy or wavelength thereby exciting only selected molecules within the carrier gas.

BRIEF DESCRIPTION OF THE DRAWINGS

So that the manner in which the above recited features, advantages and objectives of the present invention are attained and can be understood in detail, more particular description of the invention, briefly summarized above, may be had by reference to the appended drawings. It is noted, however, that the appended drawings illustrate only typical embodiments of the invention and therefore not to be considered limiting in scope, for the invention may admit to other equally effective embodiments.

DETAILED DESCRIPTION OF THE PREFERRED EMBODIMENT

The description of the preferred embodiment of the invention will be covered in two steps. The first step will comprise a description of the physical characteristics of the gas sampling apparatus. The second step will include details of the operation of the apparatus, and the principles underlying the preferred operational modes.

Figure 1:
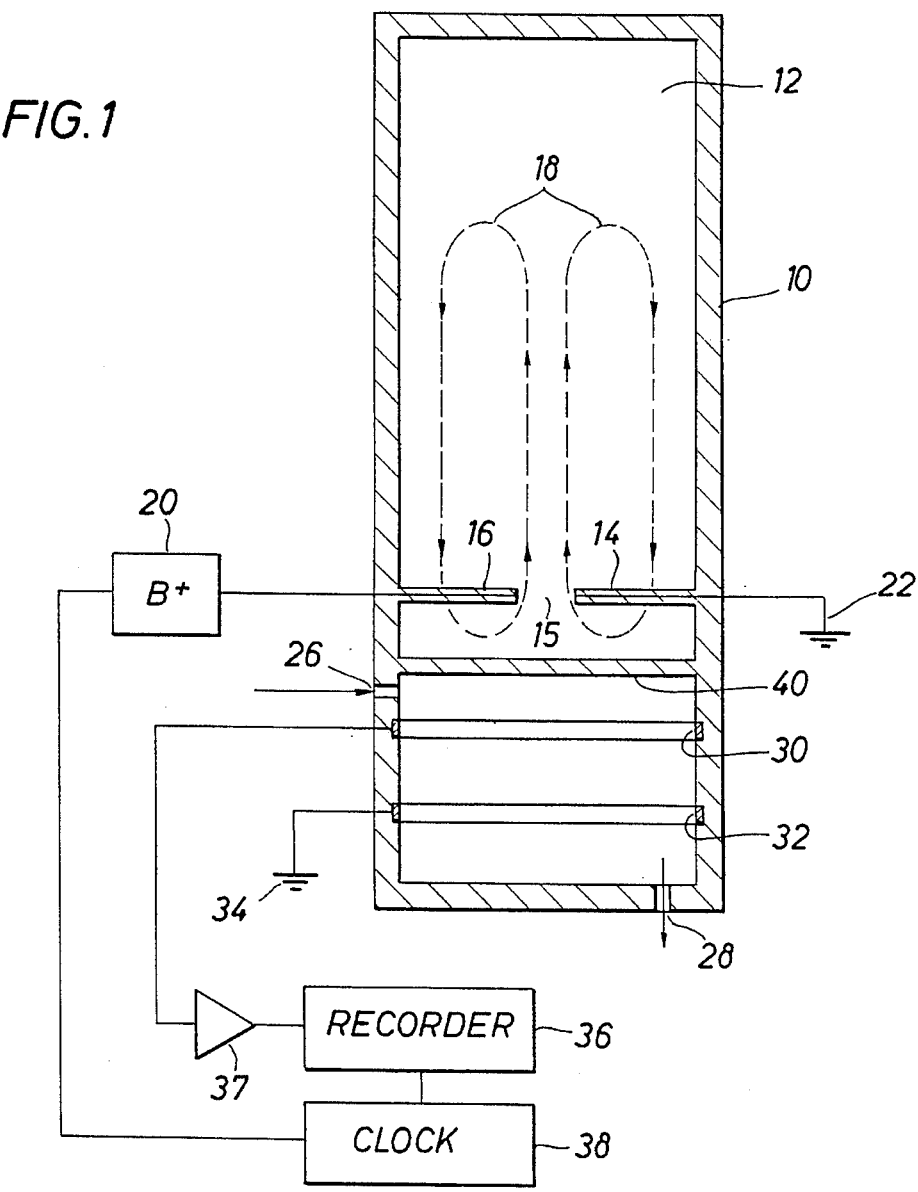
FIG. 1 is a schematic diagram of the gas sampling apparatus depicting the spark chamber, the sample chamber and major support components.

The physical characteristics of the apparatus are best illustrated by referring to FIG. 1. The numeral 10 identifies the body of the gas sampling apparatus which is formed of an insulating material such as glass or the like. The body 10 is divided into two chambers by the partition or "window" 40 forming the upper spark chamber 12 which is leak proof with respect to the surrounding atmosphere and a lower sample chamber 24. Two round and equal diameter electrodes 14 and 16 protrude inwardly from the body 10 of the detector. The tips of the electrodes are cut so as to form opposing parallel faces and are aligned with one another such that they are precisely diametrically opposite each other and thus define the spark gap 15 within the spark chamber 12. The electrodes 14 and 16 are encapsulated within the interior of the spark chamber with the same insulating material as is used to form the body 10 of the detector. The insulating material at the face of the electrodes 14 and 16 is sufficiently thick to physically isolate the electrodes from the environs of the interior of spark chamber 12 yet sufficiently thin to allow the generation of a pulsed DC spark across the spark gap 15. Electrode 16 is electrically connected to the high voltage discharge circuit 20 while the electrode 14 is grounded at point 22. The voltage applied to the electrode pair is controlled by a clock 38 in a manner detailed in a following section. In the preferred embodiment, the spark chamber 12 is filled with a gas mixture comprising helium and krypton.

Continuing the structural description of the preferred embodiment of the apparatus, attention is now drawn to the sample chamber identified in FIG. 1 by the numeral 24. Sample gas enters the sample chamber through a port 26 and exits the chamber through the port 28. A small pump or the like can be used to deliver sample gas. The sample chamber is rounded and contains circular electrodes 30 and 32 recessed within the chamber walls and exposed to the interior of the chamber. Electrode 32 is grounded at point 34. The electrode 30 is electrically connected to the recording device 36 and subsequently to a clock 38 which controls the applied positive or negative voltage as will be discussed in a following section. The electrode 32 thus has the requisite voltage to attract desired charged particles created within sample chamber 24. The partition or window 40 separating the spark chamber 12 and the sample chamber 24 is constructed of a thin membrane of magnesium fluoride ($MgF_2$) or lithium fluoride (LiF). The material and dimensions of the membrane are selected such that photoemissions at the desired energy levels generated within the spark chamber 12 experience minimal absorption in entering into the sample chamber 24. The pressure within spark chamber 12 is not critical and is set to closely match the pressure within the sample chamber 24. Stated another way, the chambers 12 and 24 are pressure balanced and therefore minimal force in the vertical direction is exerted on the window membrane 40.

Figure 2:
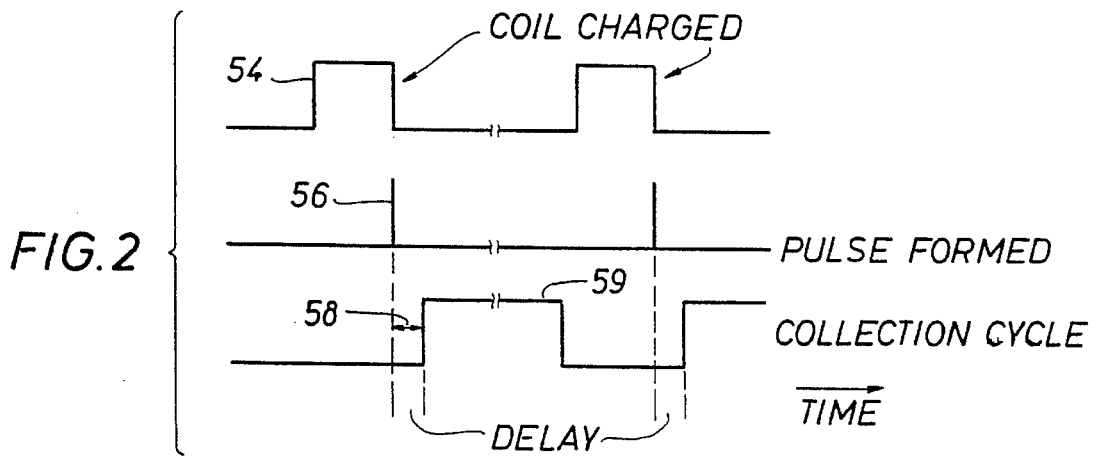
FIG. 2 is a timing chart showing the timing relationships of the charging, discharging and collection phases of the operational steps of the gas sampling apparatus.

The preferred operational embodiment is further detailed by referring to FIG. 1 and FIG. 2 in combination. The top curve in FIG. 2 shows the charging current 54 which forms the necessary charge for the operation of the high voltage discharge circuit 20. That circuit forms an output 56 which is a discharge pulse of relatively short duration across the spark gap 15. The charging-pulsing sequence is repeated sequentially under control by the clock 38. Upon discharge, the spark forms ions in the excited states as will be detailed subsequently. The discharge also elevates the temperature of the gas in the region of the spark gap 15. A temperature gradient is formed in the gas and heated, relatively buoyant gas in the spark path is evacuated by convective gas flow in an upward direction within the closed system of spark chamber 12 where it is cooled by mingling with cooler gas at the top of the chamber. Simultaneously, cooler gas replaces the heated gas in the vicinity of the spark gap 15. The net result is that the spark action creates a circulation of gas within the closed system of spark chamber 12 as depicted by the broken lines 18 in FIG. 1. This convective circulation constantly supplies "fresh" gas to the spark gap 15 resulting in the extremely long lifetime of the photoemission production without having to rely on an external supply for source gas. The spark discharge induces several reactions as discussed in the referenced U.S. Pat. No. 5,153,519 and pending applications incorporated herewithin by reference. Uses of the present invention can be expanded through the utilization of these referenced reactions. Attention will, however, be drawn to a specific reaction and the specific application of monitoring air for pollutants. The specific reaction of interest is $$Kr^* \rightarrow Kr + h\nu \tag{1}$$

where * denotes the exited state of the element krypton created within the gas mixture by the spark discharge and hv denotes photon emission resulting from the decay of krypton from the excited state to the ground state denoted by Kr. Krypton in the excited state emits photons associated with the well known resonance lines of krypton at 116.5 and 123.6 nanometers (nm) with corresponding energies of 10.03 and 10.64 electron volts (eV), respectively. A portion of this radiation passes through the window membrane 40 and into the sample chamber 24 where it interacts with the sample gas as described in the following paragraphs. The coil charging phase 54 and DC spark discharge phase 56 are repeated sequentially under the control of clock 38. Each spark creates a fresh supply of Kr* which, in turn, decays to the ground state Kr by the emission of 10.03 eV and 10.64 eV photons. Stated another way, the spark generation system in cooperation with the helium-krypton gas mixture within the closed spark chamber 12 acts as a self replenishing source of 10.03 eV and 10.64 eV radiation.

Continuing the operational description of the preferred embodiment of the invention, attention is now directed to the sample chamber 24. The sample gas enters the chamber through the port 26. The flow is preferably continuous although discrete samples may be taken and analyzed. In air pollution monitoring operations, the predominant constituent of the sample gas will, of course, be air with relatively small concentrations of pollutant compounds with one such pollutant compound being designated generically as compound AB for purposes of discussion. The gas mixture comprising air and compound AB are exposed to the photon flux of energies 10.03 and 10.64 eV generated within the spark chamber 12 and transmitted through window membrane 40. This photon flux ionizes the compound AB as described by the reaction. The gas exits the chamber through port 28.

Photons interacting with molecules of compound AB produce ions through the reaction $$h\nu + AB \rightarrow AB^+ + e^- \tag{2}$$

where $AB^+$ is a positive ion and $e^-$ denotes a free electron. The resulting flux of free electrons is collected at the electrode 30 which is at a positive potential. The positive potential is applied to the electrode 30 only after a time delay 58 to distinctly separate the spark discharge 56 and collection cycle 59. The electrode 32 which is at ground potential tends to retard ionic recombination and to repel electrons which have drifted to the lower portion of the sample chamber back toward the region of collector electrode 30. Delay time 58 and collection time 59 are controlled by clock 38. The free electron current from the electrode 30 is recorded by the recorder 36, with the magnitude of the current being proportional to the concentration of the compound AB. A measure of electron current is, therefore, an analytical measure of pollutant concentration. The delay phase 58 and collection phase 59 are repeated sequentially in synchronization with the coil charging phase 54 and spark phase 56 as shown in FIG. 2.

At this point in the discussion of the operation of the invention, the selection criterion for the gas mixture in spark chamber 12 emerges. Recall that kr* emits radiation at 10.03 and 10.64 eV. This radiation will not ionize any compound with an ionization potential above 10.64 eV. The major components of air are nitrogen with an ionization potential of 15.6 eV, oxygen with an ionization potential of 12.08 eV, water with an ionization potential of 12.6 eV and carbon dioxide with an ionization potential of 13.8 eV. If, therefore, air is the sample gas, the major constituents of air will not be ionized by the emissions from Kr*, but impurities in the air sample such as pollutants with ionization potentials below 10.64 eV will be ionized. By selecting helium as the primary component of the gas within spark chamber 12 and krypton as a secondary component in concentrations of 1.0% or less, a selective photoionization source is obtained. The major constituents of air, which if ionized would produce electron currents which would be considered as noise in trace constituent measurements, are in fact not ionized.

In summary, the invention comprises a photoemission source which has a very long life, is relatively inexpensive to manufacture and operate, requires no external source of gas and is extremely rugged. Furthermore, the preferred embodiment of the invention is directed toward, although not limited to, the quantitative analysis of air samples for trace constituents such as pollutants. The major constituents of air, in approximate percentages by volume, are nitrogen at 78%, oxygen at 21%, water ranging from a trace to 2% or more, and carbon dioxide at 0.04%. The system as described does not ionize and therefore does not directly detect these major air constituents. Only trace constituents such as organic pollutants with ionization potentials below the major air constituents are ionized and detected. Interferences from major constituents are eliminated thereby greatly increasing the sensitivity, precision and accuracy of the device for trace elements of interest.

While the foregoing disclosure is directed to the preferred embodiments of the present invention, other and further embodiments of the invention may be devised without departing from the basic scope thereof, and the scope thereof is determined by the claims which follow.

What is claimed is:

1. A method for analyzing a sample gas comprising the steps of:
   (a) exposing a first gas in a closed spark chamber to DC current across the chamber;
   (b) energizing at least one component of said first gas to an excited state as a result of exposure to said DC current and permitting the excited gas to form ionizing radiation by decay;
   (c) exposing a sample gas in a sample chamber to ionizing radiation resulting from the decay of at least one component of said first gas;
   (d) forming charged particles in said sample chamber as a result of exposure to said ionizing radiation;
   (e) measuring said charged particles wherein said measurement occurs in timed relationship to charged particle formation; and
   (f) selectively determining concentrations of compounds contained in said sample gas by utilizing said measurements.

2. The method of claim 1 wherein said first gas contained in said closed spark chamber is circulated by convective gas flow resulting from the heating of said first gas in the path of said DC current.

3. The method of claim 2 wherein said ionizing radiation is directed from said spark chamber into said sample chamber through a membrane window with minimal absorption of said ionizing radiation by said membrane window.

4. The method of claim 3 wherein pressure within said source chamber is balanced with pressure within said sample chamber.

5. The method of claim 4 wherein the energy of said ionizing radiation is below the ionization potential of the major constituents of air.

6. The method of claim 5 wherein said first gas comprises krypton and said sample gas comprises air.

7. The method of claim 6 wherein the DC current is pulsed.

8. A gas sampling apparatus comprising:

(a) a closed source chamber filled with a source gas;

(b) a sample chamber with an inlet port through which sample gas flows into the sample chamber and an outlet port through which sample gas flows out of the sample chamber;

(c) two electrodes spaced apart and protruding into said source chamber to define a spark gap across which short, repeated, high voltage pulsed DC current flows thereby raising at least one component of said source gas to an excited state;

(d) a membrane window separating said source chamber and said sample chamber through which ionizing radiation, resulting from the decay of at least one said excited component of said source gas, passes from said source chamber to said sample chamber;

(e) means of detecting charged particles formed in said sample gas resulting from the exposure of said sample gas to said ionizing radiation generated in said source chamber and passed through said membrane window into said sample chamber;

(f) means for controlling the timing of said pulsed DC current and said charged particle detection; and (g) means for converting said detected charged particles to corresponding measures of concentrations of compounds within said sample gas.

9. The apparatus of claim 8 wherein said source gas is circulated within said closed source chamber by convective gas flow resulting from the heating of said source gas in the path of said pulsed DC current across said spark gap.

10. The apparatus of claim 9 wherein said means for measuring said charged particles formed in said sample gas comprises a first electrode within said sample chamber maintained at a selected potential with respect to second electrode within said sample chamber at ground potential.

11. The apparatus of claim 10 wherein said source gas comprises krypton.

12. The apparatus of claim 11 wherein said means for controlling said pulsed DC current and said charged particle collection comprises a clock which outputs timed pulses at predetermined and sequential intervals.

13. The apparatus of claim 12 wherein said means for detecting charged particles further comprises a charge collecting circuit which cooperates with said first electrode within said sample chamber and wherein the magnitude of the current induced within said charge collecting circuit is proportional to the concentration of the component of the sample gas providing said charged particles.

14. The apparatus of claim 13 further comprising a recorder cooperating with said charge collection circuit wherein said recorder is calibrated to convert said measured current magnitude to equivalent concentration of said component of the sample gas from which said particles are generated.

15. The apparatus of claim 10 wherein said window membrane is formed of magnesium fluoride or lithium fluoride.

16. The apparatus of claim 10 wherein said sample chamber and said source chamber are pressure balanced.

17. A method for selectively analyzing a sample of air for impurities comprising the steps of:

(a) exposing a source gas comprising krypton in a closed spark chamber to DC current;

(b) energizing said krypton to an excited metastable state as a result of exposure to said current;

(c) exposing said sample of air to ionizing radiation formed by the decay of said metastable krypton within said closed spark chamber where said ionizing radiation passes from said closed spark chamber into an adjacent sample chamber through a membrane window;

(d) forming charged particles within said sample chamber by the selective ionization of impurities within said air sample while precluding the ionization of major constituents of air; and (e) determining concentrations of said impurities based upon measured magnitudes of said charged particles.

18. The method of claim 17 wherein said source gas contained in said closed spark chamber is circulated by convective gas flow resulting from the heating of said source gas by said DC current and the subsequent cooling of said gas convectively conveyed to locations within said closed spark chamber remote from said DC current.

19. The method of claim 18 including the step of directing ionizing radiation from said spark chamber into said sample chamber through a lithium fluoride or magnesium fluoride window with minimal attenuation.

20. The method of claim 18 wherein the air constituents of oxygen, nitrogen, water vapor and carbon dioxide are not energized and not detected and impurities with ionization potentials below 10.64 eV are energized and are observed.

* * * * *